United States Patent
Kanai et al.

(10) Patent No.: US 9,594,064 B2
(45) Date of Patent: Mar. 14, 2017

(54) PLATE-TYPE COLUMN, TEMPERATURE REGULATION SYSTEM AND GAS CHROMATOGRAPH SYSTEM

(71) Applicant: SHIMADZU CORPORATION, Kyoto-shi, Kyoto (JP)

(72) Inventors: Masaki Kanai, Nara (JP); Takahiro Nishimoto, Soraku-gun (JP); Masanori Nishino, Joyo (JP); Satoshi Matsuoka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 201 days.

(21) Appl. No.: 13/896,138

(22) Filed: May 16, 2013

(65) Prior Publication Data
US 2013/0333444 A1 Dec. 19, 2013

(30) Foreign Application Priority Data
May 17, 2012 (JP) .................. 2012-113571

(51) Int. Cl.
*G01N 30/90* (2006.01)
*G01N 30/30* (2006.01)
(Continued)

(52) U.S. Cl.
CPC .............. *G01N 30/90* (2013.01); *G01N 30/30* (2013.01); *G01N 30/54* (2013.01); *G01N 30/6004* (2013.01); *G01N 2030/3007* (2013.01)

(58) Field of Classification Search
CPC ........... G01N 2030/3007; G01N 30/30; G01N 30/54; G01N 30/6004; G01N 30/90
See application file for complete search history.

(56) References Cited

U.S. PATENT DOCUMENTS 5,808,178 A * 9/1998 Rounbehler et al. ......... 73/23.39
6,514,316 B1 * 2/2003 Gaisford et al. .................. 95/87
(Continued)

FOREIGN PATENT DOCUMENTS

CN 1212370 A 3/1999
CN 102262138 A 11/2011
(Continued)

OTHER PUBLICATIONS

Examination Report received for Chinese Patent Application No. 201310185144.4 mailed on May 27, 2014, 20 pages (9 pages of English Translation and 11 pages of Office Action).

*Primary Examiner* — Freddie Kirkland, III
(74) *Attorney, Agent, or Firm* — Morgan, Lewis & Bockius LLP (57) ABSTRACT

Provided is a plate-type column which allows the temperature of its inner passage to be rapidly increased or decreased while ensuring the correctness of an analysis or other operations. A plate-type column 10 includes: a plate-shaped main body 11; projecting portions 12 and 13 protruding from a circumferential edge of the main body 11; and a fluid-flow passage 14 extending in the main body 11 and the projecting portions 12 and 13. An intermediate portion of the passage 14 is provided in the main body 11, while each of the end portions of the passage 14 extends from the main body 11 through the projecting portion 12 or 13, with each of the end portions being open to the outside at the tip of the projecting portion 12 or 13.

11 Claims, 3 Drawing Sheets (51) Int. Cl.
*G01N 30/54* (2006.01)
*G01N 30/60* (2006.01)

(56) References Cited

U.S. PATENT DOCUMENTS

| | | | |
|---|---|---|---|
| 6,530,260 B1 * | 3/2003 | Mustacich et al. | 73/23.41 |
| 6,612,153 B2 | 9/2003 | White et al. | 73/23.42 |
| 8,043,565 B1 | 10/2011 | Patterson et al. | |
| 8,414,832 B1 * | 4/2013 | Roques et al. | 422/89 |
| 8,506,801 B2 * | 8/2013 | Burger et al. | 210/198.2 |
| 8,512,456 B2 * | 8/2013 | Wasson et al. | 96/101 |
| 8,591,630 B2 * | 11/2013 | Amirav et al. | 95/87 |
| 9,034,077 B2 * | 5/2015 | Amirav et al. | 95/87 |
| 2003/0037592 A1 * | 2/2003 | D'Couto et al. | 73/23.35 |
| 2012/0085148 A1 * | 4/2012 | Amirav et al. | 73/23.39 |

FOREIGN PATENT DOCUMENTS

| | | |
|---|---|---|
| JP | 2001-343377 A | 12/2001 |
| JP | 2003-021595 | 1/2003 |
| JP | 2005-140505 A | 6/2005 |
| JP | 2006-10704 A | 1/2006 |
| JP | 2011-89853 A | 5/2011 |
| WO | 2010/138693 A1 | 12/2010 |

\* cited by examiner

PLATE-TYPE COLUMN, TEMPERATURE REGULATION SYSTEM AND GAS CHROMATOGRAPH SYSTEM

TECHNICAL FIELD

The present invention relates to a plate-type column having a passage for letting a fluid (gas or liquid) flow through to separate the components in the fluid introduced into the passage, to analyze those components, to make them undergo some type of reaction, or for other purposes. It also relates to a temperature regulation system for performing a temperature regulation of the plate-type column, and a gas chromatograph system having the plate-type column and the temperature regulation system.

BACKGROUND ART

In recent years, gas chromatograph systems have been widely used for separating and/or analyzing components in a gaseous sample. There are two types of columns commonly used in gas chromatographs, i.e. a packed column, which consists of a glass or stainless-steel tube filled with a stationary phase, and a capillary column, which consists of a quartz tube with a stationary phase applied to its inner wall. In many cases, these columns are contained in a convection oven and heated in such a manner that their temperature gradually increases. Normally, the temperature of the column at the moment of sample introduction is low. As the temperature gradually increases, the components in the sample are sequentially and individually separated. When the last component is separated, the temperature reaches as high as 200 to 400° C. Accordingly, when one analysis is completed and a new sample must be introduced into the column to initiate the next analysis, it is necessary to rapidly cool the hot column and oven. However, the convection oven impedes such a rapid temperature regulation since this type of oven has a large heat capacity.

To solve this problem, in recent years, a plate-type column has been developed, which consists of a metallic or silicon substrate with a micro passage formed therein. Furthermore, a gas chromatograph system capable of rapidly increasing or decreasing the temperature of a plate-type column by pressing the column on a heater block to heat or cool it (draw heat away from it) by thermal conduction has also been proposed (for example, see Non-Patent Document 1).

BACKGROUND ART DOCUMENT

Non-Patent Document

Non-Patent Document 1: *IEEJ Transactions on Electrical and Electronic Engineering*, May 2009, Volume 4, Issue 3, pp. 358-364

SUMMARY OF THE INVENTION

Problem to be Solved by the Invention

Figure 5:
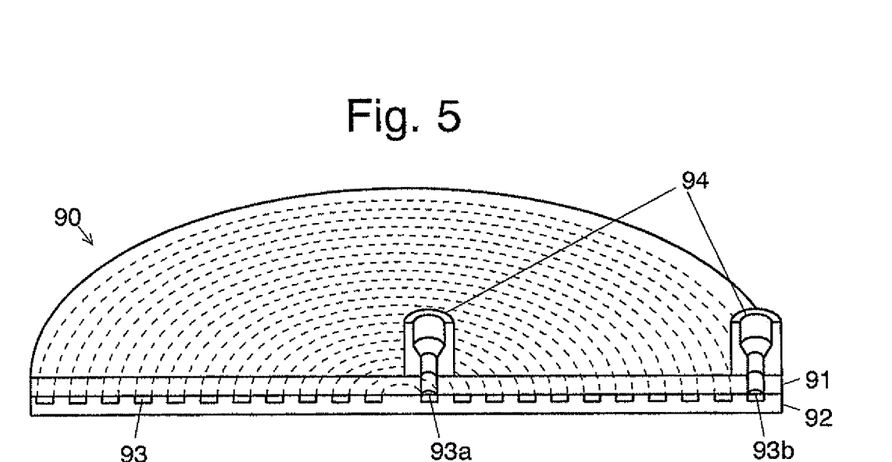
FIG. 5 is a perspective view showing one example of conventional plate-type columns.

The configuration of a plate-type column according to Non-Patent Document 1 is shown in FIG. 5. For convenience of explanation, the plate-type column according to the aforementioned document shown in this figure is cut at its center. This plate-type column has a laminated body 90 consisting of a circular glass substrate 91 and a silicon substrate 92, with a micro passage 93 spirally formed in this body 90. Both the inlet end 93*a* and the outlet end 93*b* of this passage 93 are open on the upper side of the body 90. Each of the openings is fitted with a tube connection member 94 made of an alloy or similar material. The tube connection member 94 is directly joined to the upper surface of the column body 90 by anodic bonding or other methods. By connecting a gas-introducing tube or gas-discharging tube to each tube connection member 94, the plate-type column can be inserted into the gas passage of a gas chromatograph system.

In the conventional plate-type column having the previously described configuration, the distribution of the heat capacity over the entire column is non-uniform due to the influence of the tube connection members 94 attached to the body 90 of the column. Therefore, when the temperature is rapidly increased or decreased, the temperature distribution in the passage may possibly be uneven and cause the analysis result to be incorrect.

The present invention has been developed in view of such a problem, and its objective is to provide a plate-type column which allows the temperature of its inner passage to be rapidly increased or decreased while ensuring the correctness of an analysis or other operations. The present invention also provides a temperature regulation system for regulating the temperature of such a plate-type column, and a gas chromatograph system having the plate-type column and the temperature regulation system.

Means for Solving the Problems

The plate-type column according to the present invention aimed at solving the aforementioned problem includes:
a) a plate-shaped main body;
b) a projecting portion protruding from a circumferential edge of the main body; and
c) a fluid-flow passage extending in the main body and the projecting portion,
wherein an intermediate portion of the passage is provided in the main body, while the end portions of the passage extend from the main body through the projecting portion, with each of the end portions being open to the outside at the tip of the projecting portion, thus allowing the main body and the projecting portion to individually and independently undergo a temperature regulation.

Having both ends of the fluid-flow passage open to the outside at the tip of the projecting portion (i.e. providing both the inlet and outlet of the passage at the tip of the projecting portion) allows the connection of an external tube to the passage to be made at a position apart from the main body of the plate-type column. This allows the main body to have a small, uniform heat capacity, which prevents the temperature distribution in the passage inside the main body from being uneven when the temperature of the main body is rapidly increased or decreased. The projecting portion is designed to be fitted with a tube connection member for the connection of an external tube. Although this fitting makes the distribution of the heat capacity in the projecting portion somewhat uneven, the influence of this unevenness of the heat capacity can be alleviated by forming the largest possible portion of the passage inside the main body or regulating the temperature of the projecting portion with a large time constant.

The plate-type column according to the present invention may have only a single projecting portion, with both end portions of the passage being extended through this single projecting portion. However, it is desirable to provide two or more projecting portions and extend each of the end portions of the passage through a different projecting portion. As compared to the configuration having both end portions of the passage formed in the same projecting portion, the present configuration allows each of the projecting portions to be smaller in width, which is advantageous for impeding heat conduction between the main body and the projecting portions.

In the plate-type column according to the present invention, the main body and the projecting portion may be created as separate members. However, it is preferable to form both the main body and the projecting portion on the same member, with a portion of this member being cut off to form the projecting portion. This design allows the plate-type column to be inexpensively produced by simple machining.

For the temperature regulation of the aforementioned plate-type column, the present invention aimed at solving the aforementioned problem also provides a temperature regulation system, including:

a) a first temperature regulator for regulating the temperature of the main body;

b) a second temperature regulator for regulating the temperature of the projecting portion; and c) a controller for individually and independently controlling the first temperature regulator and the second temperature regulator.

With this temperature regulation system, the main body and the projecting portion of the plate-type column can be individually and independently subjected to a temperature regulation. Therefore, it is possible to control the system so that the temperature of the main body, whose heat capacity is comparatively uniform, is regulated with a relatively small time constant, whereas the temperature of the projecting portion, whose heat capacity is comparatively non-uniform, is regulated with a relatively large time constant.

A gas chromatograph system according to the present invention aimed at solving the aforementioned problem includes the aforementioned temperature regulation system and the aforementioned plate-type column with a stationary phase for gas chromatography being supported on an inner wall of the passage.

Effect of the Invention

As described thus far, in the plate-type column, the temperature regulation system and the gas chromatograph system according to the present invention, even if the temperature is rapidly increased or decreased, a substantially uniform temperature distribution is created over the entire area of the passage in the main body. Therefore, the throughput of an analysis or other operations can be improved without affecting the result of the analysis or the like.

BRIEF DESCRIPTION OF THE DRAWINGS

FIGS. 1A and 1B are schematic configuration diagrams of a plate-type column according to one embodiment of the present invention, where FIG. 1A is a plan view and FIG. 1B is a sectional view at line X-X in FIG. 1A.

BEST MODE FOR CARRYING OUT THE INVENTION

One mode for carrying out the present invention is hereinafter described by means of an embodiment.

Figure 1A:
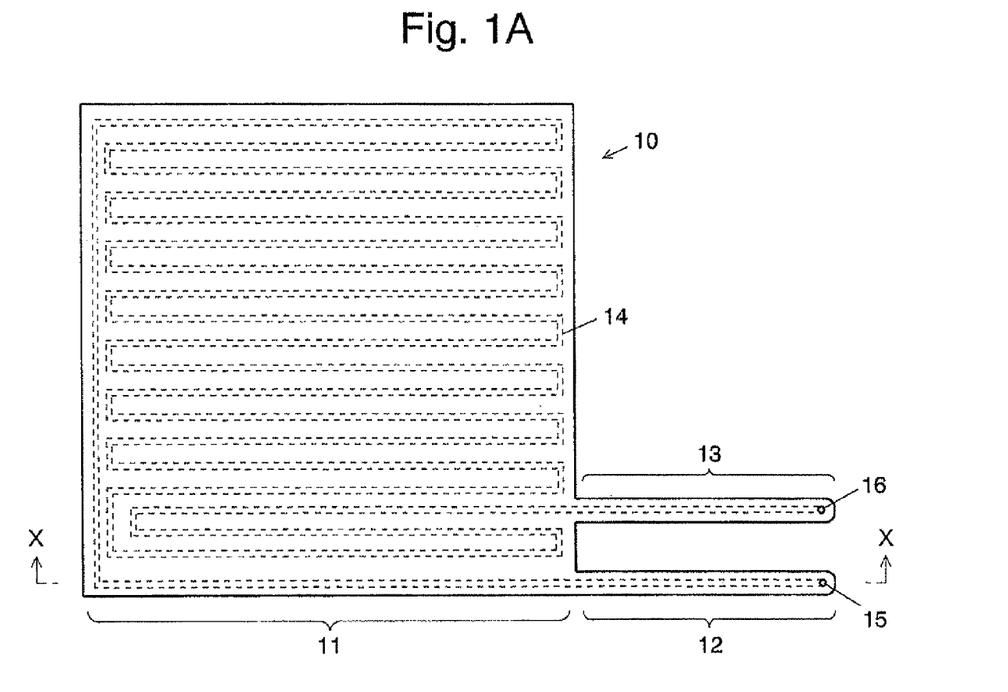
Figure 1B:
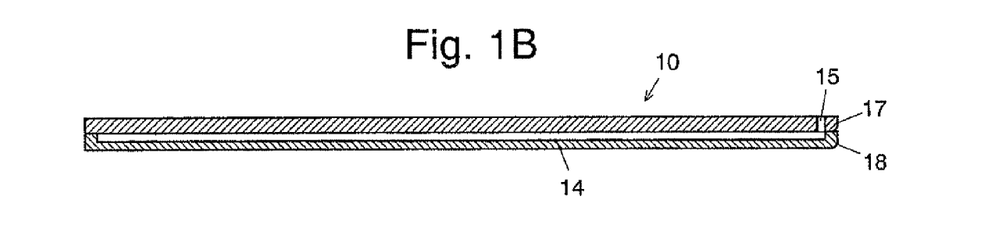

FIGS. 1A and 1B are configuration diagrams of a plate-type column according to one embodiment of the present invention. The plate-type column 10 has a rectangular main body 11 as well as first and second projecting portions 12 and 13 protruding from one side of the main body 11. Both the first and second projecting portions 12 and 13 are smaller in width than the main body 11.

The main body 11, the first projecting portion 12 and the second projecting portion 13 consist of two stainless substrates of 0.3 mm in thickness (which are hereinafter called the upper substrate 17 and the lower substrate 18) laminated to each other. The main body 11 measures 10 cm in length and 10 cm in width. Each of the first and second projecting portions 12 and 13 is 3-8 cm in length and 0.6 cm in width.

The plate-type column 10 has an inner passage 14 of 100-200 μm in width, 50-100 μm in depth, and 7-8 m in length. The intermediate portion of the passage 14 is formed in the main body 11. The end portions of the passage 14 respectively extend from the main body 11 through the first and second projecting portions 12 and 13. First and second openings 15 and 16, each of which serves as either an inlet or outlet for a fluid, are respectively provided at the tips of the first and second projecting portions 12 and 13. Through the first and second openings 15 and 16, the passage 14 communicates with an external space at both ends. The passage 14 in the plate-type column 10 should be designed so that the largest portion thereof (at least one half) is included in the main body 11. For this purpose, the passage 14 in the present embodiment is folded multiple times inside the main body 11, as shown in FIGS. 1A and 1B.

It should be noted that the aforementioned sizes and materials are mere examples and do not limit the present invention. For example, various materials can be used to create the upper and lower substrates 17 and 18, such as a metal other than stainless, glass, silicon or resins. It is also possible to create each of the upper and lower substrates 17 and 18 from a different material.

A method for producing the plate-type column 10 according to the present embodiment is hereinafter described. Initially, a groove, which will be the passage 14, is formed on one side of the lower substrate 18, while two through-holes, which will be the first and second openings 15 and 16, are formed in the upper substrate 17. The two substrates are arranged parallel to each other, with the groove-formed surface on the inside. After the through-holes are aligned with the ends of the groove, the two substrates are laminated to each other by adhesion, brazing or other methods. Then, both the upper and lower substrates 17 and 18 are simultaneously punched to obtain the previously described shape having the main body 11, the first projecting portion 12 and the second projecting portion 13.

For the plate-type column 10 produced in the previously described manner to serve as a separation column for gas chromatography, it is necessary to apply a liquid phase for gas chromatography (a stationary-phase liquid) to the surface of the passage 14. Furthermore, before the application of the liquid phase, it is preferable to perform a modifying process on the passage surface in order to inactivate adsorption sites present on the passage surface as well as to improve the wettability (i.e. degree of wetting) of the liquid phase on the passage surface. Specifically, this can be achieved as follows: Initially, a glass coating material is poured into the passage 14 from the first or second opening 15 or 16 of the plate-type column 10 to coat the passage surface with that material, after which a silane coupling agent is poured to modify the passage surface. Then, the liquid phase is poured into the surface-modified passage 14. As a result, the liquid phase is supported on the surface of the passage 14.

Figure 2:
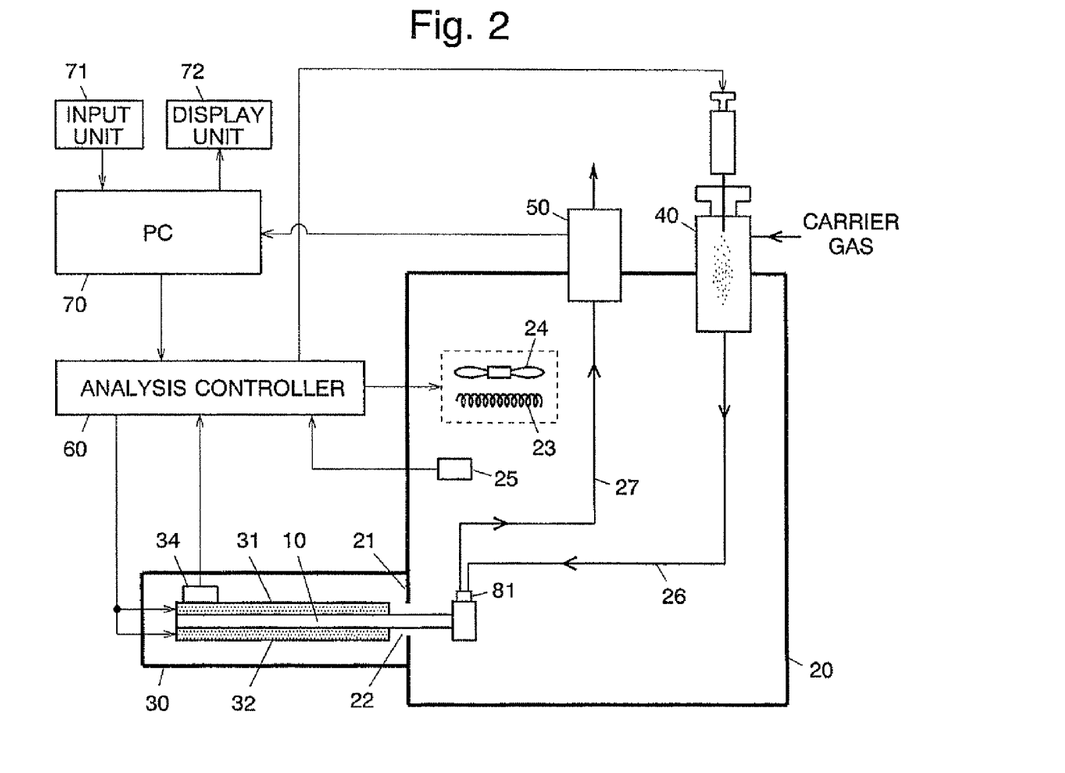
FIG. 2 is a schematic diagram showing the configuration of the main components of a gas chromatograph system according to the embodiment.
Figure 3:
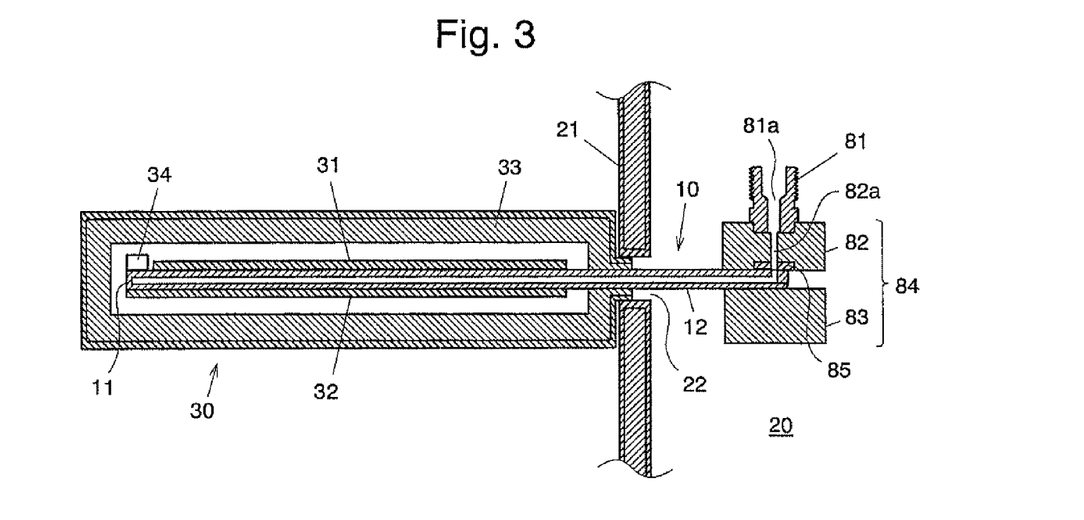
FIG. 3 is an enlarged sectional view of the plate-type column and surrounding portions of the aforementioned gas chromatograph system.

A gas chromatograph system according to one embodiment of the present invention is hereinafter described with reference to FIGS. 2 and 3. FIG. 2 is a schematic configuration diagram of the gas chromatograph system according to the present embodiment. FIG. 3 is an enlarged sectional view of the plate-type column and surrounding portions of the present gas chromatograph system. The gas chromatograph system according to the present embodiment is a system for analyzing a sample by using the plate-type column 10 having the previously described configuration. Similar to conventional gas chromatograph systems, it includes an oven 20, a sample vaporizing chamber 40 and a detector 50, as well as a plate temperature regulator 30 for regulating the temperature of the main body 11 of the plate-type column 10. The present gas chromatograph system further includes an analysis controller 60 for controlling the operations of the aforementioned components and a personal computer 70 ("PC" in FIG. 2) which controls the analysis controller 60 and processes detection signals produced by the detector 50.

In the gas chromatograph system according to the present invention, the plate temperature regulator 30 corresponds to the first temperature regulator in the present invention, while the oven 20 corresponds to the second temperature regulator. The analysis controller 60 corresponds to the controller in the present invention.

The plate temperature regulator 30 is located next to the oven 20. Its inner space communicates with that of the oven 20 through an opening 22 formed in the wall 21 of the oven 20. When the plate-type column 10 is in use its main body 11 is contained in the plate temperature regulator 30, while its first and second projecting portions 12 and 13 protrude through the opening 22 into the oven 20. A pair of plate-shaped heaters 31 and 32, each of which consists of a ceramic heater, mica heater, rubber heater or similar type of heater, are provided parallel to each other in the plate temperature regulator 30. The main body 11 of the plate-type column 10 is placed between the plate-shaped heaters 31 and 32, whereby the main body 11 is heated. The inner wall surface of the plate temperature regulator 30 is covered with a heat insulator 33. A first temperature sensor 34 for measuring the temperature of the main body 11 is attached to the upper surface of the plate-type column 10 at a position inside the plate temperature regulator 30. Unlike the present configuration having two plate-shaped heaters 31 and 32 on both sides of the main body 11, the system may be provided with only one plate-shaped heater on either the upper or the lower side of the main body 11.

The oven 20 is a convection type which is commonly used in gas chromatograph systems. It contains a heater 23 for heating the air inside and a fan 24 for agitating the heated air. A second temperature sensor 25 for measuring the temperature inside the oven 20 is also provided. As stated earlier, the first and second projecting portions 12 and 13 of the plate-type column 10 are to be inserted into this oven 20. The oven 20 also contains a first tube 26 for introducing a gaseous sample and a carrier gas from the sample vaporizing chamber 40 and sending them to the plate-type column 10, and a second tube 27 for sending sample components from the plate-type column 10 to the detector 50.

A tube connection member 81 for connecting the first or second tube 26 or 27 to the first or second opening 15 or 16 of the plate-type column 10 is attached to each of the first and second projecting portions 12 and 13. The tube connection member 81 may be directly joined onto the surface of the plate-type column 10 by adhesion, brazing or other methods. However, it is more preferable to design the tube connection member 81 so that it can be freely attached to and removed from the plate-type column 10. This design allows the tube connection members 81 to be connected to the first and second projecting portions 12 and 13 of the plate-type column 10 after the first and second projecting portions 12 and 13 are inserted from the side of the plate temperature regulator 30 into the oven 20 through the opening 22 formed in the wall 21. This is advantageous for reducing the vertical size of the opening 22 so as to suppress the transfer of heat between the plate temperature regulator 30 and the oven 20.

One example of the configuration using a tube connection member 81 that can be freely attached or removed is shown in FIG. 3. In this example, the tube connection member 81 is provided on a block-shaped member (which is hereinafter called the "connector block 84"). This connector block 84 serves as an adapter for attaching the tube connection member 81 to the first or second projecting portion 12 or 13. The connector block 84 consists of upper and lower blocks 82 and 83, with the tube connection member 81 being fitted on the upper side of the upper block 82. This upper block 82 has a through-hole formed in its central portion as a passage 82a. The upper end of this passage 82a communicates with a through-hole 81a formed in the central portion of the tube connection member 81. A procedure for attaching the connector block 84 to the plate-type column 10 is as follows: Initially, a gasket 85 made of a metal or similar material is placed around each of the first and second openings 15 and 16 of the plate-type column 10, after which the upper and lower blocks 82 and 83 are positioned so as to clamp the tip portion of the first or second projecting portion 12 or 13 from above and below. Then, the upper and lower blocks 82 and 83 are clamped toward each other by a clamp mechanism (not shown). As a result, the gasket 85 becomes flattened, creating a hermetical connection between the passage 14 in the plate-type column 10 and the passage 82a in the upper block 82.

Information about the temperatures detected with the first temperature sensor 34 in the plate temperature regulator 30 and the second temperature sensor 25 provided in the oven 20 is sent to the analysis controller 60. Under the supervision of the personal computer 70, the analysis controller 60 controls the operations of each of the components of the gas chromatograph system. Based on the aforementioned temperature information, the analysis controller 60 appropriately controls the plate-shaped heaters 31 and 32 in the plate temperature regulator 30 as well as the heater 23 and the fan 24 in the oven 20 so that the temperatures of the plate temperature regulator 30 and that of the oven 20 will respectively be adjusted to the temperatures specified by the personal computer 70.

An input unit 71 for allowing users to give various commands or set analysis conditions and a display unit 72 for showing various kinds of information, such as the set analysis conditions, the progress of an analysis or the result of the analysis, are connected to the personal computer 70. By executing a dedicated controlling and processing software program installed on the personal computer 70, various controls and processes can be performed.

In the gas chromatograph system according to the present embodiment, either a constant temperature analysis, in which the temperature is maintained at the same level throughout the analysis, or a temperature-increasing analysis, in which the temperature is increased in the course of the analysis, is performed depending on the kinds of components contained in the sample or other factors. In any of these analyses, the temperature control of the plate temperature regulator 30 and the oven 20 is conducted according to a temperature profile previously set in the personal computer 70.

In the case of a constant temperature analysis, the analysis controller 60 controls the plate-shaped heaters 31 and 32 in the plate temperature regulator 30 as well as the heater 23 and the fan 24 in the oven 20 so that the values detected with the first and second temperature sensors 34 and 25 will be maintained at constant values respectively specified in the temperature profile. In the case of a temperature-increasing analysis, the analysis controller 60 controls the plate-shaped heaters 31 and 32 in the plate temperature regulator 30 so that the detection value of the first temperature sensor 34 will gradually increase as specified in the temperature profile, while controlling the heater 23 and the fan 24 in the oven 20 so that the detection value of the second temperature sensor 25 will be maintained at a constant value specified in the temperature profile. To prevent liquefaction of high-boiling components in the sample, the temperature in the oven 20 should be set higher (e.g. by 5-10° C.) than the highest temperature to be achieved by the plate temperature regulator 30.

A detailed procedure of a temperature-increasing analysis by the gas chromatograph system according to the present embodiment is hereinafter described. Initially, a predetermined quantity of sample solution is injected into the sample vaporizing chamber 40. The thereby gasified sample is conveyed by the carrier gas into the first tube 26 and passes through the tube connection member 81, to be introduced from the first opening 15 into the passage 14 in the plate-type column 10. In this process, the oven 20 is maintained at a high temperature (e.g. 410° C.) which exceeds the boiling points of the components in the sample. Therefore, the components in the gasified sample can reach the main body 11 without being adsorbed onto the first tube 26 or the passage 14 in the first projecting portion 12. At the beginning of the analysis, the plate temperature regulator 30 is controlled to have a comparatively low temperature (e.g. 50-100° C.), the gasified sample which has flown into the main body 11 is temporarily trapped in the passage 14 and condensed. Then, as the temperature of the plate temperature regulator 30 is gradually increased, the sample components begin to flow in the passage 14 in ascending order of their boiling points. After passing through the main body 11 and the second projecting portion 13, the components exit from the second opening 16 into the second tube 27. The components in the sample will be completely discharged from the plate-type column 10 before the plate temperature regulator 30 reaches a predetermined maximal temperature (e.g. 400° C.). The discharged components flow through the second tube 27, to be eventually detected by the detector 50. Since the oven 20 is still maintained at the aforementioned high temperature, even the component having the highest boiling point can reach the detector 50 without being adsorbed onto the passage 14 in the second projecting portion 13 or the second tube 27 after exiting from the main body 11.

Thus, in the gas chromatograph system according to the present embodiment, the tube connection members 81 for connecting the passage 14 in the plate-type column 10 and external tubes (i.e. the first and second tubes 26 and 27) can be attached at a position apart from the main body 11 which contains the largest portion of the passage 14. This design allows the main body 11 of the plate-type column 10 to have a small, uniform heat capacity, so that a substantially uniform temperature distribution can be created over the entire area of the passage 14 even if the temperature of the main body 11 is rapidly increased or decreased. Thus, the throughput of the analysis can be improved without affecting the result of the analysis. Another favorable effect is that placing the tube connection members 81 outside the plate temperature regulator 30 allows reducing the thickness of the plate temperature regulator 30. This design decreases the heat capacity of the plate temperature regulator 30 and allows the temperature to be more quickly increased or decreased. The amount of power consumed for the temperature regulation of the column will also be decreased.

The first and second projecting portions 12 and 13 are fitted with the tube connection members 81, and therefore, have large, non-uniform heat capacities. However, this causes no serious problem since these portions are located in the oven 20 and their temperature is regulated with a larger time constant than used for the main body 11.

The thin shape of the first and the second projecting portions 12 and 13 impedes the heat conduction between the main body 11 and the projecting portions 12 and 13. Therefore, even when the temperature of the main body 11 is regulated to be different from that of the first and second projecting portions 12 and 13, they will not significantly influence each other.

One mode for carrying out the present invention has been described thus far by means of an embodiment. It should be noted that the present invention is not limited to the previous embodiment, which can be appropriately changed within the spirit of the present invention. For example, unlike the previous embodiment in which the plate-type column 10 has two projecting portions (the first and second projecting portions 12 and 13) extending from the main body 11 with the inlet and outlet ends of the passage 14 respectively formed in the two projecting portions 12 and 13, it is possible to create a plate-type column having only one projecting portion, with both the inlet and outlet portions of the passage formed in that projecting portion.

Figure 4:
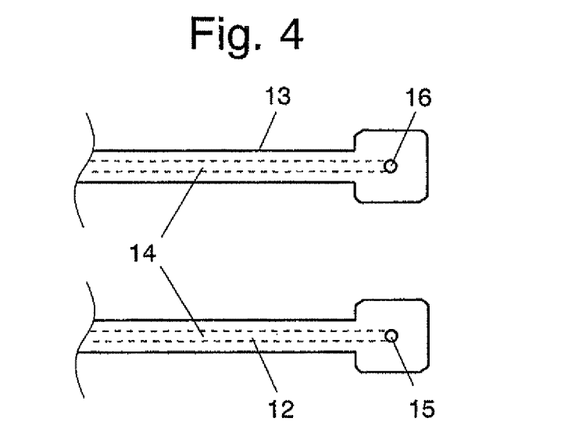
FIG. 4 is a plan view showing another example of the shape of the projecting portions.

In the example of FIGS. 1A and 1B, the first and second projecting portions 12 and 13 have almost the same width from base to tip. However, this is not the only possible form. For example, it is possible to make their tip portion wider than the other portion, as shown in FIG. 4. In this case, the tip portion must be wide enough for a tube connection member to be attached thereto (e.g. 0.6 cm or greater), whereas, from the viewpoint of suppressing the heat conduction between the main body 11 and the projecting portions, the other portion should preferably be as thin as possible within the range where the passage 14 can be formed in it (e.g. approx. 0.6 mm).

In the previous example, the main body and the projecting portions are integrally created. However, they can also be created as separate members. One possible example is the structure consisting of a plate-shaped member as the main body and tubular members as the projecting portions, with both ends of the inner passage of the main body being open on one side surface of the main body, and the tubular members respectively joined to these open ends. When separate members are thus used as the main body and the projecting portions, it is possible, for example, to create the main body from a metal or similar material having a comparatively high thermal conductivity and the projecting portions from quartz or a similar material having a comparatively low thermal conductivity. On the other hand, when the main body and the projecting portions are integrally created, it is possible to create the projecting portions by an inexpensive process, such as punching or wire-cutting, so that the entire part can be created at a lower cost than in the case of using separate members which require the joining process.

In the previous example, the projecting portions are extended along the same plane as the main body. However, this is not the only possible design. It is possible to extend the projecting portions in a direction intersecting with the aforementioned plane.

The plate-type column according to the present invention can be used not only as a plate-type column for gas chromatography but also as a so-called microreactor, i.e. a substrate having an inner passage in which a fluid is made to undergo some reaction, or a flow cell consisting of a substrate having an inner passage which a fluid is passed through to be detected with a predetermined type of detector. In general, the plate-type column can be applied to any device which uses a substrate having an inner passage for allowing a fluid to flow through so as to separate components in the fluid, analyze those components or make them undergo some reaction. Similarly, the temperature regulation system according to the present invention can be applied to not only the temperature regulation of a plate-type column in a gas chromatograph system but also the temperature regulation of the aforementioned various kinds of devices.

EXPLANATION OF NUMERALS

10 . . . Plate-Type Column
11 . . . Main Body
12 . . . First Projecting Portion
13 . . . Second Projecting Portion
14 . . . Passage
15 . . . First Opening
16 . . . Second Opening
17 . . . Upper Substrate
18 . . . Lower Substrate
20 . . . Oven
23 . . . Heater
24 . . . Fan
25 . . . Second Temperature Sensor
26 . . . First Tube
27 . . . Second Tube
30 . . . Plate Temperature Regulator
31, 32 . . . Plate-Shaped Heater
33 . . . Heat Insulator
34 . . . First Temperature Sensor
40 . . . Sample Vaporizing Chamber
50 . . . Detector
60 . . . Analysis Controller
70 . . . Personal Computer
81 . . . Tube Connection Member
84 . . . Connector Block

The invention claimed is:

1. A plate type column, comprising:
a) a plate-shaped main body; and
b) a projecting portion protruding from a circumferential edge of the main body, the plate-shaped main body and the projecting portion forming therein a groove as a fluid-flow passage extending in the main body and the projecting portion,
wherein an intermediate portion of the passage is provided in the main body, while end portions of the passage extend from the main body through the projecting portion, with each of the end portions being open to an outside at a tip of the projecting portion, thus allowing the main body and the projecting portion to individually and independently undergo a temperature regulation, and
wherein two or more projecting portions are provided for the main body, and each of the end portions of the passage is extended through a different projecting portion.

2. The plate-type column according to claim 1, wherein both the main body and the projecting portion are formed on a same member, with a portion of this member being cut off to form the projecting portion.

3. The plate-type column according to claim 1, wherein a stationary phase for gas chromatography is supported on an inner wall of the passage.

4. The plate-type column according to claim 1, wherein the main body and the projecting portion consist of two substrates laminated to each other and the groove is formed on one side of one of the two substrates.

5. The plate-type column according to claim 4, wherein a through-hole for communicating with an external space is formed in the projecting portion of another substrate of the two substrates.

6. The plate-type column according to claim 1, wherein:
the main body is sandwiched with a pair of plate-shaped heaters and a temperature of the main body is regulated by the pair of plate-shaped heaters; and
a temperature of the projecting portion is regulated by an oven.

7. A temperature regulation system for regulating a temperature of the plate type column including: a plate-shaped main body; a projecting portion protruding from a circumferential edge of the main body, the plate-shaped main body and the projecting portion forming therein a groove as a fluid-flow passage extending in the main body and the projecting portion, where an intermediate portion of the passage is provided in the main body, while end portions of the passage extend from the main body through the projecting portion, with each of the end portions being open to an outside at a tip of the projecting portion, the temperature regulation system comprising:
a) a first temperature regulator for regulating a temperature of the main body;
b) a second temperature regulator for regulating a temperature of the projecting portion; and
c) a controller for individually and independently controlling the first temperature regulator and the second temperature regulator,
wherein two or more projecting portions are provided for the main body, and each of the end portions of the passage is extended through a different projecting portion.

8. A gas chromatograph system comprising:
a plate-type column including:
a plate-shaped main body; and
a projecting portion protruding from a circumferential edge of the main body, the plate-shaped main body and the projecting portion forming therein a groove as a fluid-flow passage extending in the main body and the projecting portion, where-an intermediate portion of the passage is provided in the main body, while end portions of the passage extend from the main body through the projecting portion, with each of the end portions being open to an outside at a tip of the projecting portion, and a stationary phase for gas chromatography is supported on an inner wall of the passage; and a temperature regulation system including:
a first temperature regulator for regulating a temperature of the main body;
a second temperature regulator for regulating a temperature of the projecting portion; and
a controller for individually and independently controlling the first temperature regulator and the second temperature regulator,
wherein two or more projecting portions are provided for the main body, and each of the end portions of the passage is extended through a different projecting portion.

9. The gas chromatograph system according to claim 8, wherein:

the second temperature regulator is a convection-type oven including a heater and a fan, and the projecting portion is contained in the oven; and
the first temperature regulator is a plate temperature regulator which is located next to the oven, an inner space of the plate temperature regulator communicates with an inner space of the oven through an opening formed in a wall of the oven, and the main body is contained in the plate temperature regulator.

10. The gas chromatograph system according to claim 9, wherein the plate temperature regulator includes two plate-shaped heaters which sandwich the main body.

11. The gas chromatograph system according to claim 9, wherein:

the oven further includes a first tube for sending a gaseous sample and a carrier gas introduced from a sample vaporizing chamber to the plate-type column, a second tube for sending sample components from the plate-type column to a detector, and a tube connection member for connecting the projecting portion, the first tube, and the second tube.

* * * * *